(12) United States Patent
Shi et al.

(10) Patent No.: US 7,728,135 B2
(45) Date of Patent: Jun. 1, 2010

(54) SYNTHESIS OF CCR5 RECEPTOR ANTAGONISTS

(75) Inventors: Xiongwei Shi, Edison, NJ (US); Man Zhu, Clark, NJ (US); William Leong, Westfield, NJ (US); Vilas Dahanukar, Hyderabad (IN); Ilia A. Zavialov, Princeton, NJ (US); Cecelia Proietti, Clark, NJ (US); Shannon Zhao, Littleton, MA (US); Hong-Chang Lee, Livingston, NJ (US); Yi Liu, Clark, NJ (US); Hoa N. Nguyen, Dayton, NJ (US); Wenxue Wu, Princeton Junction, NJ (US); Bosco D'Sa, Edison, NJ (US); Feng Liang, Monmouth Junction, NJ (US); Loc Thanh Tran, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 1003 days.

(21) Appl. No.: 11/326,154

(22) Filed: Jan. 5, 2006

(65) Prior Publication Data

US 2006/0258863 A1    Nov. 16, 2006

Related U.S. Application Data

(60) Provisional application No. 60/641,900, filed on Jan. 6, 2005.

(51) Int. Cl.
*C07D 401/14* (2006.01)
*C07D 403/12* (2006.01)
*A61K 31/506* (2006.01)
*A61K 31/18* (2006.01)

(52) U.S. Cl. .................. 544/295; 544/364; 544/335

(58) Field of Classification Search ................ 544/335, 544/295, 364
See application file for complete search history.

(56) References Cited

U.S. PATENT DOCUMENTS 6,720,325 B2    4/2004    Miller

FOREIGN PATENT DOCUMENTS

WO    WO96/26196 A    8/1996

OTHER PUBLICATIONS

International Search Report for PCT/US2006/000262; mailed Jun. 21, 2006.

*Primary Examiner*—Venkataraman Balasubramanian
(74) *Attorney, Agent, or Firm*—Patent Practitioners of Schering Corporation

(57) ABSTRACT

The present invention is directed to the synthesis of 4-[4-[(R)-[1-[cyclopropylsulfonyl)-4-piperidinyl](3-fluorophenyl)methyl]-3(S)-methyl-1-piperazinyl]-1-[(4,6-dimethyl-5-pyrimidinyl)carbonyl]-4-methylpiperidine], and intermediates therefor from readily available starting materials by a novel route.

36 Claims, No Drawings

SYNTHESIS OF CCR5 RECEPTOR ANTAGONISTS

CROSS REFERENCE TO PRIORITY APPLICATION

This application claims the benefit of priority to U.S. provisional application Ser. No. 60/641,900 filed Jan. 6, 2005.

FIELD OF THE INVENTION

This application concerns the synthesis of the CCR5 receptor antagonist 4-[4-[(R)-[1-[cyclopropylsulfonyl)-4-piperidinyl](3-fluorophenyl)methyl]-3(S)-methyl-1-piperazinyl]-1-[(4,6-dimethyl-5-pyrimidinyl)carbonyl]-4-methylpiperidine.

BACKGROUND OF THE INVENTION

4-[4-[(R)-[1-[cyclopropylsulfonyl)-4-piperidinyl](3-fluorophenyl)methyl]-3(S)-methyl-1-piperazinyl]-1-[(4,6-dimethyl-5-pyrimidinyl)carbonyl]-4-methylpiperidine] has the structure shown below (Formula I):

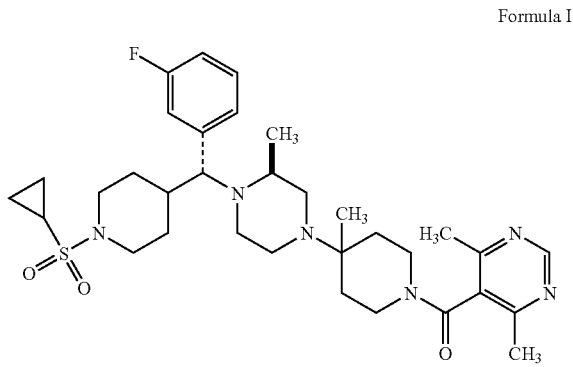

Formula I

The compound of Formula I is an antagonist of the CCR5 receptor and is useful for the treatment of AIDS and related HIV infections. CCR5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease. This compound is described and claimed in U.S. Pat. No. 6,720,325, the disclosure of which is incorporated herein by reference.

Reference is also made to patent application Ser. No. 11/326,155, filed concurrently herewith which relates to certain rotamer salts.

In view of the importance of antagonists of the CCR5 receptor, new, novel methods of making such antagonists are always of interest.

SUMMARY OF THE INVENTION

In one embodiment, the present application teaches a novel process of making a compound of formula I. The compound of formula I is prepared from a compound of formula V:

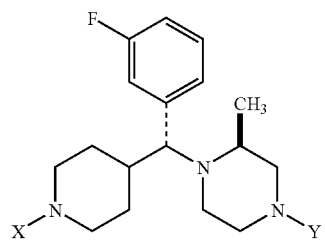

V where X is selected from the group consisting of: p-methoxybenzyl (PMB), allyl, methoxymethyl, benzyloxymethyl, trityl, pivaloyloxymethyl, tetrahydranyl, benzyl, di(p-methoxyphenyl)methyl, triphenylmethyl, (p-methoxyphenyl) diphenylmethyl, and t-butyl carbamate ("t-Boc"); and Y is selected from the group consisting of: carbobenzyloxy (Cbz), $CZ_3CO$ (where Z is a halogen), 2-trimethylsilylethyl carbamate, 1-methyl-1-phenylethyl carbamate, t-butyl carbamate, cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, methyl carbamate, ethyl carbamate, diphenylphosphinyl, benzenesulfenyl, RCO (where R is $C_{1-6}$alkyl), benzoyl, and other common acyl groups, with the proviso that X and Y are not the same group (e.g., both X and Y are not t-Boc simultaneously) since the inventive process utilizes the differentiation of X and Y under the reaction conditions employed in the invention, e.g., X can be selectively removed without affecting Y.

The inventive process comprises the sequential steps of:

(a) selectively removing the X protecting group of the compound of formula V to produce a compound of formula VI:

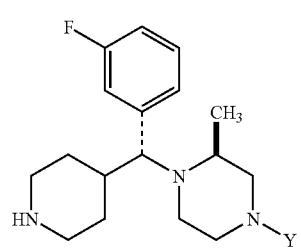

VI (b) sulfonylating the compound of formula VI with

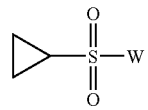

is where W=a halide or triflate, to form the compound of formula VII:

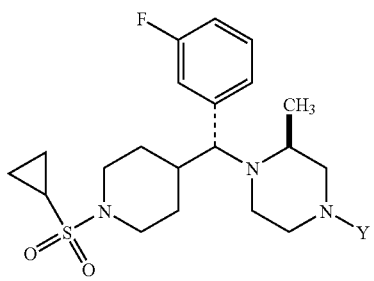

(c) removing the Y protecting group from the compound of formula VII and then reacting with hydrogen bromide to produce the di-hydrobromide salt formula VIII:

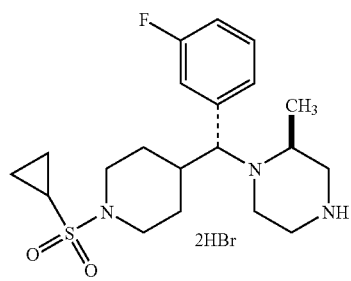

(d) reacting the compound of formula VIII with (i) an agent containing a leaving group G, where G is a leaving group selected from the group consisting of CN, Z, $OSO_2R^1$, $OCOCZ_3$ and benzotriazolyl, with $R^1$ being an alkyl or aryl group and Z is a halogen, and (ii) the compound:

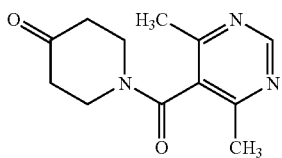

to form the compound of formula IX:

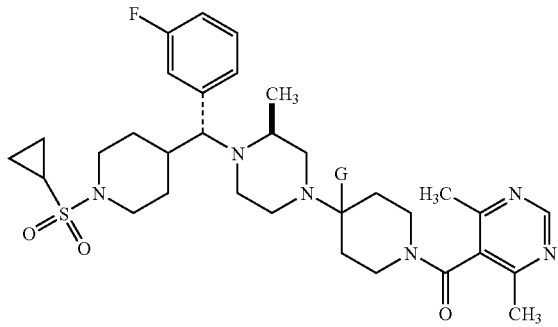

and (e) reacting the compound of formula IX with a Grignard reagent in a suitable solvent, followed by a workup, to yield the compound of formula I.

The inventive process to make the compound of formula I has numerous advantages including it is economical and can be easily scaled-up.

DESCRIPTION OF THE INVENTION

Except where stated otherwise, the following definitions apply throughout the present specification and claims. These definitions apply regardless of whether a term is used by itself or in combination with other terms.

"Acyl" means an H—C(O)—, alkyl-C(O)—, cycloalkyl-C(O)—, or aryl-C(O)— and the like. The bond to the parent moiety is through the carbonyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkylsulfonate" means an alkyl-S(O$_2$)—O— group in which the alkyl group is as previously described. Preferred groups are those in which the alkyl group is lower alkyl. The bond to the parent moiety is through the oxygen.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Cbz" means carbobenzyloxy.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms.

"Halide" means fluoro, chloro, bromo or iodo.

"Halogen" means fluoro, chloro, bromo or iodo.

"Heterocyclic" means a non-aromatic saturated monocyclic or multicyclic ring system comprising about 3 to about 10 ring atoms, preferably about 4 to about 7 ring atoms, in which one or more of the atoms in the ring system is an element other than carbon, for Preparative Example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(cbz), —N(Tos) group and the like; such protections are also considered part of this invention.

"PMB" means p-methoxybenzyl.

"Triflate" means trifluoromethanesulfonyl.

In one embodiment, the present invention discloses a novel, easy-to-use process for preparing the compound of formula I. The process comprises:

(a) converting the compound of formula II:

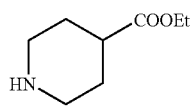

to a compound of formula III by reaction with a reagent that introduces a group X:

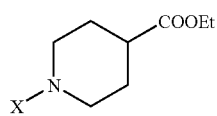

where X is selected from the group consisting of: p-methoxybenzyl (PMB), allyl, methoxymethyl, benzyloxymethyl, trityl, pivaloyloxymethyl, tetrahydranyl, benzyl, di(p-methoxyphenyl)methyl, triphenylmethyl, (p-methoxyphenyl)diphenylmethyl and t-Boc, and is preferably p-methoxybenzyl (PMB);

(b) reacting the compound of formula III with a suitable reducing reagent, followed by purification through formation of a bisulfite salt and subsequent treatment with a base, to yield a compound of formula IV:

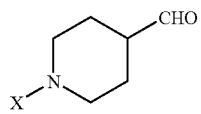

(c) reacting the compound of formula IV with (i) the compound of formula:

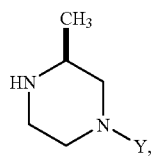

and (ii) a compound selected from the group consisting of benzotriazole, a nitrile, a halide, an alkylsulfonate, a haloalkyl sulfonate and a haloalkyl acid, preferably benzotriazole, and (iii) 3-fluorophenylmagnesium bromide, to yield a compound of formula V:

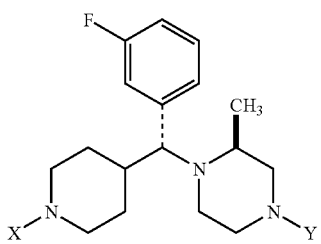

where Y is selected from the group consisting of: carbobenzyloxy (Cbz), $CZ_3CO$ (where Z is a halogen), 2-trimethylsilylethyl carbamate, 1-methyl-1-phenylethyl carbamate, t-butyl carbamate, cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, methyl carbamate, ethyl carbamate, diphenylphosphinyl, benzenesulfenyl, RCO (where R is $C_{1-6}$alkyl), benzoyl and other common acyl groups, and is preferably carbobenzyloxy (Cbz), with the proviso that X and Y are different such that X may be selectively removed;

(d) removing the X protecting group of the compound of formula V to produce a compound of formula VI:

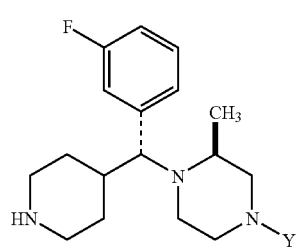

(e) sulfonylating the compound of formula VI with a cyclopropyl

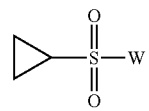

sulfonyl moiety, where W is a halide or triflate, to form the compound of formula VII:

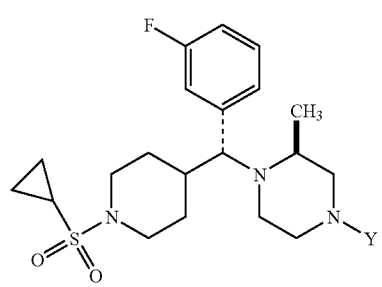

(f) removing the Y protecting group from the compound of formula VII and reacting with hydrogen bromide to produce the di-hydrobromide salt formula VIII:

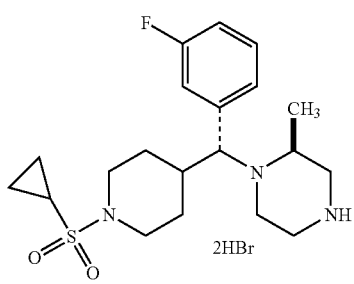

VIII

· 2HBr (g) reacting the compound of formula VIII with an agent containing a leaving group G where G is a leaving group preferably selected from the group consisting of CN, Z, OSO$_2$R$^1$, OCOCZ$_3$ and benzotriazolyl, with R$^1$ being an alkyl or aryl group and Z is a halogen; and the compound of Formula VIIIa:

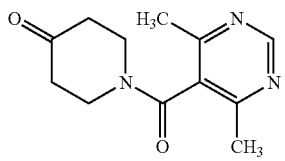

Formula VIIIa to form the compound of formula IX:

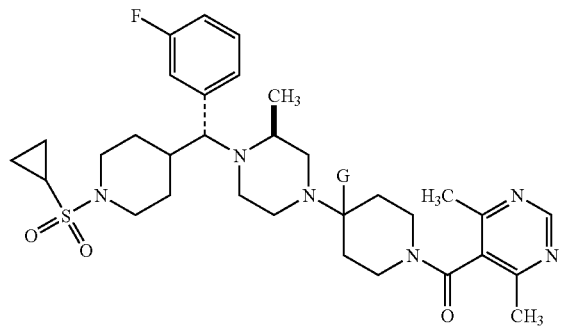

IX and (h) reacting the compound of formula IX with a Grignard reagent in a suitable solvent to yield the compound of formula I.

As stated above, X and Y are not the same moiety since X and Y are to be differentiated under the reaction conditions employed.

The preferred protecting group for X is p-methoxybenzyl (PMB):

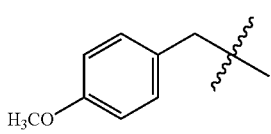

p-Methoxybenzyl (PMB)

The preferred protecting group for Y is carbobenzyloxy (Cbz):

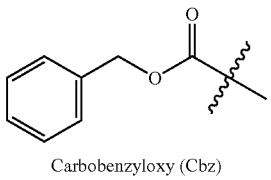

Carbobenzyloxy (Cbz)

Protecting groups are sometimes named as carbamates herein for convenience; for example Cbz could be referred to as benzyl carbamate and so forth.

The deprotection in step (d) is performed using 2,3-dichoro-5,6-dicyano-1,4-benzoquinone or trifluoroacetic anhydride. Preferably, the deprotection is performed using trifluoroacetic anhydride.

The preferred W in step (e) is Cl.

The deprotection in step (f) is performed using strong acids such as sulfuric acid, hydrochloric acid, hydrobromic acid, methanesulfonic acid and the like. Preferably, the protection is accomplished using methanesulfonic acid.

The reaction in step (g) comprises (1) converting compound of formula VIII to a free base by use of a basic compound and (2) reacting free base with an agent containing a leaving group G and the compound of Formula VIIIa:

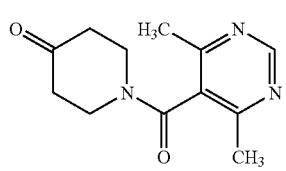

Formula VIIIa where G is a leaving group preferably selected from the group consisting of CN, Z, OSO$_2$R$_2$, OCOCZ$_3$ and benzotriazolyl, with R$_2$ being an alkyl or aryl group and Z is a halogen.

The term "an agent containing a leaving group G" refers to a compound that upon reaction as shown herein, leaves a moiety G described above on the compound being reacted. Thus, the above-noted phrase "where G is a leaving group preferably selected from the group consisting of CN, Z, OSO$_2$R$_2$, OCOCZ$_3$ and benzotriazolyl" means that the compound (agent) contains in it as bonded moiety CN, Z, OSO$_2$R$_2$, OCOCZ$_3$ or benzotriazolyl, and then leaves the CN, Z, OSO$_2$R$_2$, OCOCZ$_3$ or benzotriazolyl upon being reacted with the compound of Formula VIII to form the compound of Formula IX as a result of said reaction. The more preferred agent containing a leaving group is a cyanating agent and is selected from the group consisting of: HCN, acetone cyanohydrin; cyclohexanone cyanohydrin; a mixture of (C$_2$H$_5$)$_2$ AlCN and Ti(OPr)$_4$, a mixture of acetic acid, H$_2$SO$_4$; NaHSO$_4$, KHSO$_3$ or Na$_2$S$_2$O$_5$ and a cyanide source such as NaCN or KCN; trimethylsilylcyanide; glycolonitrile; mandelonitrile; glycinonitrile; acetone amino nitrile; and dimethylaminoacetonitrile. Most preferably, the cyanating agent is acetone cyanohydrin.

The acetone cyanohydrin is used in about 1-5 molar equivalents with respect to the compound of formula VIII.

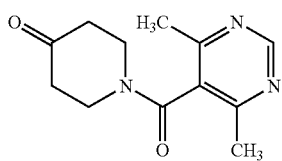

Formula VIIIa

The compound of Formula VIIIa is used in about 1-4 molar equivalents with respect to the compound of formula VIII.

The basic compound in step (g) is selected from the group consisting of a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium; a metal salt of a $C_1$-$C_{12}$ alkanol, a $C_3$-$C_{12}$ cycloalkanol, a ($C_3$-$C_8$ cycloalkyl)$C_1$-$C_6$ alkanol; ammonia, a $C_1$-$C_{12}$ alkylamine, a di($C_1$-$C_{12}$ alkyl)amine, a $C_3$-$C_8$ cycloalkylamine, a N—($C_3$-$C_8$ cycloalkyl)-N—($C_1$-$C_{12}$ alkyl)amine, a di($C_3$-$C_8$ cycloalkyl)amine, a ($C_3$-$C_8$ cycloalkyl)$C_1$-$C_6$ alkylamine, a N—($C_3$-$C_8$-cycloalkyl)$C_1$-$C_6$-alkyl-N—($C_1$-$C_{12}$ alkyl)amine, a N—($C_3$-$C_8$ cycloalkyl)$C_1$-$C_6$ alkyl-N—($C_3$-$C_8$ cycloalkyl)amine, a di[($C_1$-$C_6$ cycloalkyl)$C_1$-$C_6$ alkyl[amine; and a heterocyclic amine selected from the group consisting of imidazole, triazole, pyrrolidine, piperidine, heptamethyleneimine, morpholine, thiomorpholine and a 1-($C_1$-$C_4$ alkyl)piperazine.

Preferably, the basic compound is selected from the group consisting of KOH, NaOH, $Na_2CO_3$, $K_2CO_3$, $NaHCO_3$, $KHCO_3$, tetramethylguanidine, DBU, diisopropylethylamine and mixtures thereof. More preferably, the basic compound is $Na_2CO_3$ or $K_2CO_3$. Most preferably, the basic compound is $K_2CO_3$.

The Grignard reagent in step (h) is selected from the group consisting of MeMgCl, MeMgBr and MeMgI and is most preferably MeMgCl.

The MeMgCl is used in about 1-4 molar equivalents with respect to the compound of formula IX.

The solvent in step (h) is selected from the group consisting of toluene, xylene, chlorobenzene, or dichlorobenzene alone or in admixture with a solvent selected from the group consisting of a $C_5$-$C_{12}$ alkyl ether, 1,2-dimethoxyethane, 1,2-diethoxyethane, diglyme, 1,4-dioxane and tetrahydrofuran. The preferred solvent is a mixture of toluene and tetrahydrofuran.

The work-up in step (h) is treatment with an acid such as sulfuric acid, hydrochloric acid, phosphoric acid, and the like, in an aqueous phase and is preferably hydrochloric acid.

In another embodiment, the application teaches a method for the preparation of a compound of formula V from a compound of formula IV:

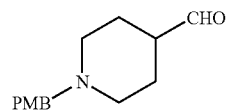

IV wherein the process comprises reacting the compound of formula IV with (i) benzotriazole, nitriles, halogens, alkylsulfonates or haloalkyl esters, preferably benzotriazole; (ii) 3-fluorophenylmagnesium bromide, and (ii) the compound:

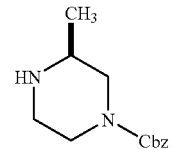

in a suitable solvent to yield a compound of formula V.

The solvent is selected from the group consisting of hydrocarbons, halogenated hydrocarbons, ethers, and mixtures thereof, and is preferably a mixture of toluene and tetrahydrofuran.

The inventive process is schematically described in Scheme I:

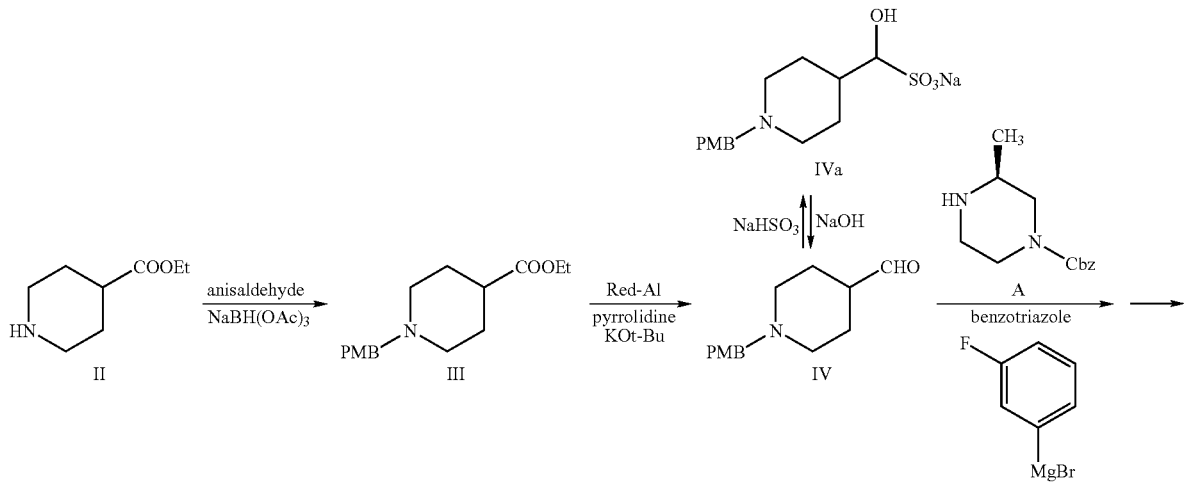

Scheme 1

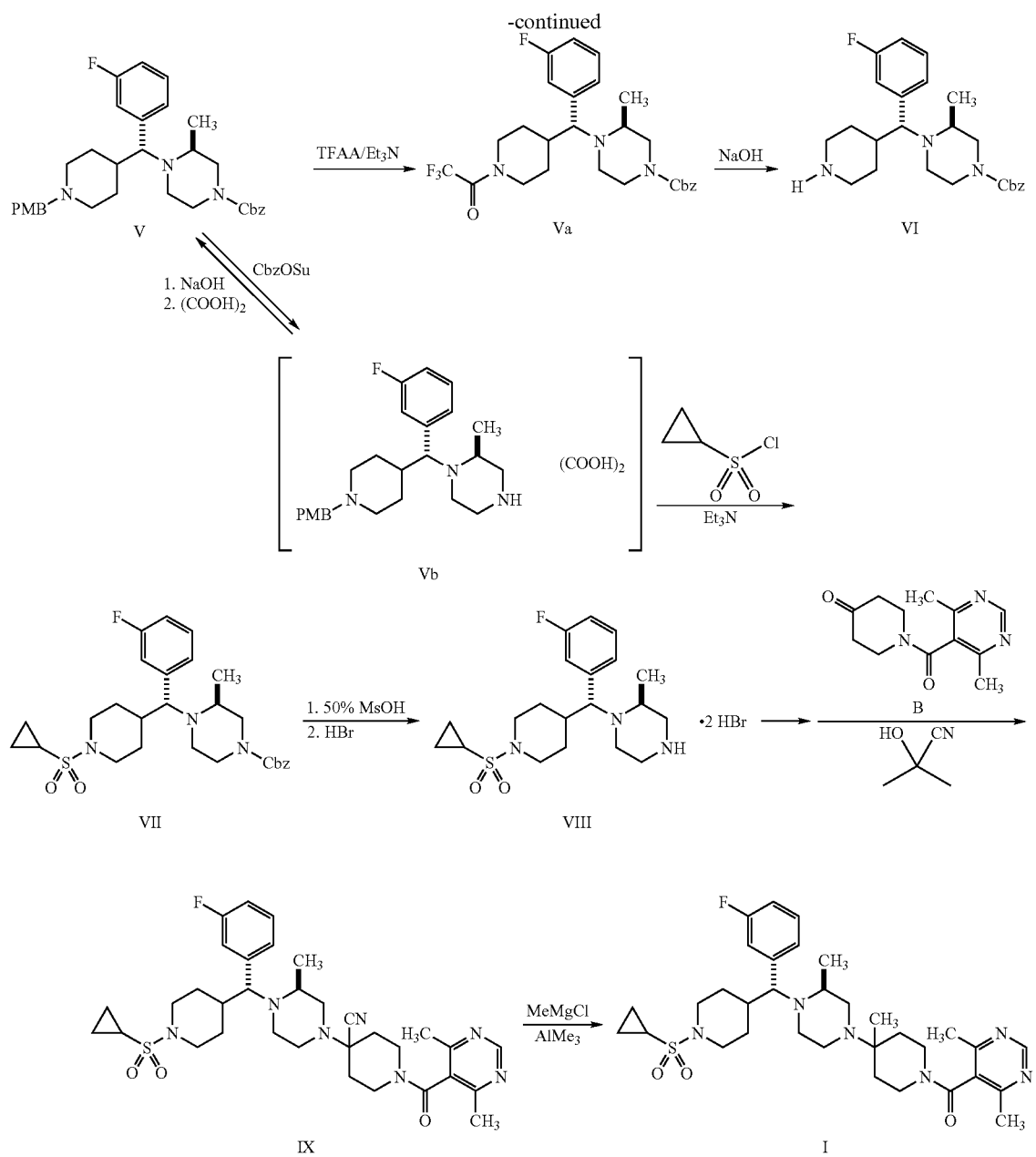

The term "alkyl" refers to a monovalent group derived from a straight or branched chain saturated hydrocarbon by the removal of a single atom having from 1 to 8 carbon atoms, preferably from 1 to 6. The term "aryl" represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl and 2-naphthyl, and especially phenyl. The term "halogen" represents fluorine, chlorine, bromine and iodine.

If desired, the compound of formula I may be further converted to the CCR5 antagonist of formula X by suitable procedures known to those skilled in the art.

The products of the various steps in the reaction schemes described herein may be isolated and purified by conventional techniques is such as, for example, filtration, recrystallization, solvent extraction, distillation, precipitation, sublimation and the like, well known to those skilled in the art. The products may be analyzed and/or checked for purity by conventional methods well known to those skilled in the art such as, for example, thin layer chromatography, NMR, HPLC, melting point, mass spectral analysis, elemental analysis and the like.

The following nonlimiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:

$CDCl_3$=Deuterochloroform

Cbz=carbobenzyloxy

DSC=Differential Scanning Calorimetry

DMSO=dimethylsulfoxide

EtOH=ethanol g=grams

HCl=hydrochloric acid

HPLC=High Performance Liquid Chromatography

M.pt: melting point

MHz=megahertz mL=milliliters

MS=Mass Spectrum

MTBE=methyl t-butyl ether

NaOH=sodium hydroxide

NMR=nuclear magnetic resonance spectroscopy

PMB=p-methoxybenzyl

THF=tetrahydrofuran

Example 1

Preparation of Compound of formula III from a compound of formula II: Compound III is prepared from compound II and p-anisaldehyde via reductive amination. Compound II (50 g, 318 mmol) is added to a stirred slurry of sodium triacetoxyborohydride (101.1 g, 1.5 equiv) in anhydrous tetrahydrofuran (500 mL). p-Anisaldehyde (45.5 g, 1.05 equiv) is next added to the batch slowly at a batch temperature below 25° C. The mixture is stirred for about 16 hours at room temperature. Upon completion the reaction is quenched with the addition of water (150 mL), and THF is removed via vacuum distillation. MTBE and water are added to the batch followed by pH adjustment to 1.5-2.5 with hydrochloric acid. The batch is filtered to remove boric acid before splitting the layers. The product containing aqueous layer is washed with MTBE. After splitting, fresh MTBE is charged to aqueous layer followed by pH adjustment to 9-11 with sodium hydroxide. After splitting, the aqueous layer is charged with MTBE, the mixture is filtered and the phases are separated. The combined organic layers are concentrated and diluted with toluene. The batch is concentrated under vacuum to a final volume of 150 mL. This solvent displacement provides III in about 90-95% yield as an approximately 50% solution in toluene. The product solution is filtered to remove residual solids and is used directly in the next step. For oxalate salt of compound III: $^1$H NMR (400 MHz, DMSO-$d_6$) δ 7.41 (m, 2H), 6.92 (m, 2H), 4.11 (br, 4H), 3.80 (s, 3H), 3.20 (br, 2H), 2.82 (br, 2H), 2.61 (s, 1H), 2.05 (d, J=6.5 Hz, 2H), 1.85 (br, 2H), 1.21 (t, J=7.1 Hz, 3H); $^{13}$C NMR (100.6 MHz, DMSO-$d_6$) δ 173.5, 164.6, 160.1, 132.7, 123.2, 114.4, 60.6, 59.1, 55.5, 50.4, 39.2, 38.2, 25.5, 14.4; MS (ESI) for M+H calcd. 278. found 278.

Example 2

Preparation of Compound of formula IV from a compound of formula III: Literature reference: Abe, T.; Haga, T.; Negi, S.; Morita, Y.; Takayanagi, K.; Hamamura, K. *Tetrahedron*, 2001, 57, 2701.

The modified Red-Al reagent is prepared according to the above literature reference: Red-Al solution (150 mL, 70 wt % in toluene) is charged to a clean reaction vessel under nitrogen. MTBE (180 mL) is added to dilute the reagent and the batch is cooled to −25° C. Pyrrolidine (52 mL) is slowly charged to the batch maintaining the temperature below −5° C. The batch is warmed to 25° C. and agitated for 10 hours. A slurry of potassium t-butoxide (4.3 g) in THF (12 mL) is added and the mixture is agitated for 1 hour to give the modified Red-Al reagent.

To a solution of III in toluene (containing 100 g active, 360 mmole) diluted with MTBE (100 mL) is slowly charged the above modified Red-Al reagent at a temperature below 10° C. Batch is agitated at 5-10° C. until the reaction completion is indicated by GC analysis. Batch is cooled to −5° C. and quenched first with a solution of sodium citrate dihydrate (120 g) in water (400 mL), followed by addition of an aqueous solution of citric acid to adjust pH to 8-9 range. The product containing organic layer is washed with water. The crude product aldehyde IV is extracted from organic layer with two washes of aqueous sodium bisulfite. The pH of combined bisulfite extracts is adjusted to 9-10 using potassium carbonate (approx. 120 g) in water (250 mL). The precipitated bisulfite salt IVa is collected by filtration and washed with MTBE. A sample of the bisulfite salt was dried to give a white solid. $^1$H NMR (400 MHz, DMSO-$d_6$) δ 7.14 (d, J=8.4 Hz, 2H), 6.81 (d, J=8.4 Hz, 2H), 4.82 (d, J=5.3 Hz, 1H), 3.68 (s, 3H), 3.57 (t, J=5.2 Hz, 1H), 3.27 (s, 2H), 2.71 (br d, J=10.9 Hz, 2H), 1.62 (m, 5H), 1.25 (m, 2H).

The wet bisulfite salt IVa is suspended in MTBE (300 mL) at 25° C. and treated with 25% NaOH (250 mL) for 1 hour. After split, product containing organic layer is concentrated and the solvent is exchanged to toluene to a final volume of 300 mL. The solution of III in toluene is used directly in the next step. A purified sample of IV gives the following spectral data: $^1$H NMR (400 MHz, $CDCl_3$): δ 9.65 (s, 1H), 7.25 (m, 2H), 6.82 (m, 2H), 3.82 (s, 3H), 3.41 (s, 2H), 2.82 (m, 2H), 2.25 (m, 1H), 2.15 (m, 2H), 1.91 (m, 2H), 1.70 (m, 2H). MS (ESI) for M+H calcd. 234. found 234.

Example 3

Preparation of Compound of formula V from compounds of formula IV and A: Benzotriazole (57.0 g), toluene (1 L) and solution of A (105.5 g active) in toluene are charged to vessel equipped with a Dean-Stark collection apparatus under nitrogen. A solution of IV (100.0 g active, 429 mmol) in toluene is charged keeping the batch temperature below 30° C. The batch is heated to reflux (110-120° C.) and agitated until water collection in the Dean-Stark trap is complete. The batch is atmospherically concentrated and a sample is taken to check for reaction completion by NMR and batch KF. The batch is further concentrated under vacuum to 300 mL. Anhydrous THF (1800 mL) is added at 50-60° C. and the batch is cooled to 15° C. A solution of 3-fluorophenylmagnesium bromide in THF (643 mL of 1.0 M solution) is slowly charged to the batch keeping the batch temperature below 25° C. Upon reaction completion by HPLC, the batch is quenched at 0° C. by adding a solution of sodium citrate in water (100 mL, 22 wt %) and the organic layer is concentrated to 800 mL by atmospheric distillation. The batch is cooled to 25° C. and MTBE (800 mL) is added followed by a solution of sodium citrate in water (500 mL, 22 wt %) are added. The batch is warmed up to 35° C. and agitated for 15 min. The aqueous layer is extracted with fresh MTBE (500 mL). Organic layers are combined, washed with sodium hydroxide (400 mL, 2.0 N) to remove benzotriazole and finally concentrated to 400 mL. The prepared solution of V is kept warm at 50-60° C. to avoid solidification and used directly in the next step. A purified sample of V gives the following spectral data: $^1$H NMR (400 MHz, CDCl$_3$) of a purified sample of V: δ 7.20 (m, 9H), 6.75 (m, 4H), 5.01 (m, 2H), 3.65 (s, 3H), 3.51 (d, J=8.1 Hz, 1H), 3.36 (s, 2H), 2.81 (br, 2H), 2.58 (br, 1H), 1.85 (m, 5H), 1.20 (m, 2H), 1.05 (br, 4H). MS (ESI) for M+H calcd. 546. found 546.

Example 4

Preparation of Compound of formula VI from compound of formula V: A solution of V (109 g, 199 mmol) is cooled to 0° C. and triethylamine (56 mL) is added. Trifluoroacetic anhydride (56 mL) is added slowly to the batch keeping the temperature below 10° C. The batch is warmed to 20° C. and agitated for 1 hour. A sample is taken to check for reaction completion by HPLC. Batch is cooled to 0° C. and water (300 mL) is charged keeping the temperature below 10° C. Batch is agitated for 30 min, settled, and aqueous layer is split to waste. The organic layer is a solution of compound Va. A purified sample of Va gives the following spectral data: $^1$H NMR (400 MHz, CDCl$_3$): δ 7.32 (m, 6H), 6.85 (m, 3H), 5.05 (br, 2H), 4.69 (m, 1H), 4.45 (m, 1H), 4.05 (br, 3H), 3.75 (m, 1H), 3.20 (m, 3H), 2.74 (m, 2H), 2.25 (br, 2H), 1.75 (s, 2H), 1.45 (m, 2H), 1.20 (m, 3H). MS (ESI) for M+H calcd. 522.2. found 522.2.

The above solution of Va is charged with benzyl triethylammonium chloride (15 g) and 25% sodium hydroxide solution (200 g). The batch is heated to 55° C. and agitated for 3 hours. A sample is taken to check for reaction completion by HPLC. The batch is cooled to 20° C., settled and aqueous layer is split to waste. The pH is adjusted to 0-1 with hydrochloric acid. Batch is agitated at 25° C. for 1 hour, settled, and the product containing aqueous layer was split and washed twice with isopropyl acetate to remove non-basic impurities. THF (250 mL) and MTBE (250 mL) were charged to the batch, followed by pH adjustment to 11-12 with sodium hydroxide. Product containing organic layer was washed with 20% sodium chloride solution (300 mL). The solvent is exchanged to toluene, the batch is azeotropically dried and concentrated to 500 mL. The prepared solution of VI in toluene was used directly in the next step. A purified sample of VI gives the following spectral data: $^1$H NMR (400 MHz, CDCl$_3$) δ 7.35 (m, 5H), 7.25 (m, 1H), 6.96 (m, 1H), 6.90 (m, 1H), 6.85 (m, 1H), 5.10 (br, 2H), 3.90 (br, 2H), 3.67 (m, 1H), 3.15 (m, 1H), 3.01 (m, 2H), 2.70 (br, 4H), 2.20 (m, 5H), 1.32 (m, 1H), 1.21 (m, 4H), 1.05 (m, 1H). MS (ESI) for M+H calcd. 426. found 426.

Example 5

Optional Purification of Compound of formula V via compound of formula Vb: A warm solution of V (80 g active, 147 mmol) is diluted with EtOH (1000 mL) and concentrated atmospherically to a final volume of 700 mL. Batch is cooled to 25° C. and aqueous solution of NaOH (170 mL, 50 wt %) is charged keeping the batch temperature below 40° C. The batch is heated to reflux and agitated at reflux for about 6 hours until the conversion is complete by HPLC. The batch is cooled to 25° C. and concentrated under vacuum to a volume of about 300 mL. Water (600 mL) and MTBE (500 mL) are added to the batch, temperature is adjusted to 30-40° C. After agitation, settling and split, the aqueous layer is extracted with fresh MTBE (200 mL), and organic layers are combined. The product is back-extracted with dilute hydrochloric acid at pH~5-6. The aqueous layer is washed with fresh MTBE, diluted with MTBE (500 mL), and the batch pH is adjusted to 12-14 with sodium hydroxide. Aqueous layer is split, extracted with fresh MTBE (500 mL). The combined organic layers are washed with water and concentrated by atmospheric distillation to 400 mL volume and cooled to 40° C. Isopropyl alcohol is charged (1600 mL) and the batch is concentrated by atmospheric distillation to 1200 mL volume. Batch is cooled to 25° C. and treated with activated carbon (10 g, DARCO®) at reflux for 2 hours. The batch is cooled to 25° C., filtered through celite pad, followed by wash of celite cake with isopropyl alcohol (200 mL). The filtrate is concentrated by atmospheric distillation to 500 mL volume and diluted with fresh isopropyl alcohol (700 mL). Solution of oxalic acid (40 g) in isopropyl alcohol (200 mL) is added keeping the batch temperature below 30° C. MTBE (1500 mL) is added and the batch is heated to reflux and agitated for 4 hours. The batch is cooled to 20° C. and precipitated product is filtered. The cake is washed with isopropyl alcohol/MTBE mixture (400 mL, 1:1 v/v) and dried under vacuum with nitrogen purge at 70-80° C. to give 140.0 g of Vb as an off-white solid. m.p.: 194° C. by DSC. $^1$H NMR (400 MHz, CDCl$_3$) δ 7.31 (m, 2H), 6.93 (m, 1H), 6.82 (m, 4H), 6.65 (m, 1H), 3.52 (d, J=10.1 Hz, 1H), 3.41 (s, 2H), 3.33 (s, 3H), 2.97 (m, 1H), 2.71 (m, 1H), 2.55 (m, 2H), 2.35 (m, 2H), 2.10 (m, 1H), 1.95 (m, 1H), 1.79 (m, 2H), 1.70 (m, 1H), 1.4 (m, 1H), 1.2 (m, 2H). MS (ESI) for M+H calcd. 412. found 412.

Solid compound Vb (100 g, 199 mmol) and N-(benzyloxycarbonyloxy) succinimide (53 g) are charged to a reaction vessel under nitrogen atmosphere. THF (300 mL) and water (300 mL) are added and batch is agitated at 25° C. for 30 min. Batch is then warmed to 35° C. and agitated for an additional 3 hours. A sample is taken to check for reaction completion by HPLC. Toluene (500 mL) is charged to the batch. A solution of potassium carbonate (200 g) in water (200 mL) is charged slowly maintaining batch temperature below 20° C. Batch pH is adjusted to a range of 9-11. The lower aqueous layer is split and extracted with toluene (300 mL). Organic layers are combined, washed with water and concentrated by atmospheric distillation to 450 mL volume to give a solution of V.

Example 6

Preparation of Compound of formula VIII from compound of formula VI: To a solution of compound VI (100 g active, 235 mmol) is charged toluene (500 mL) and triethylamine (28 g) and the batch is cooled to 0° C. Cyclopropyl sulfonyl chloride (36.5 g) is added keeping the batch temperature below 10° C. The batch is agitated at 0° C. for 2 hours and sampled for reaction completion. Batch is washed with a solution of 10% acetic acid in water (200 mL) to give a solution of VII in toluene. A purified sample of VII gives the following spectral data: $^1$H NMR (400 MHz, CDCl$_3$): δ 7.28 (m, 6H), 6.95 (m, 1H), 6.87 (m, 1H), 6.78 (m, 1H), 5.05 (br, 2H), 3.85 (d, J=12 Hz, 2H), 3.65 (m, 2H), 2.80 (m, 5H), 2.25 (m, 3H), 1.15 (m, 6H), 0.95 (m, 3H); $^{13}$C NMR (100.6 MHz, DMSO-d$_6$) δ 171.1, 163.9, 161.4, 154.8, 138.0, 136.6, 129.6, 128.5, 128.0, 124.8, 114.4, 67.0, 60.3, 51.5, 46.5, 46.3, 35.2, 29.7, 25.6, 21.0, 14.1, 4.2. MS (ESI) for M+H calcd. 530. found 530.

To the above solution is added a solution of methanesulfonic acid (250 mL) in water (250 mL) keeping the temperature below 30° C. The batch is warmed to 50° C., agitated for 30 min, settled and product containing aqueous layer is split. The organic layer is washed with methanesulfonic acid (250 mL) in water (250 mL). The combined aqueous layers are heated at 100° C. for 15-20 hours. A sample is taken to check for reaction completion by HPLC. Batch is cooled to 25° C. and toluene (500 mL) is added, followed by slow addition of 50% sodium hydroxide (100 mL). Batch is agitated for 15 min and a sample is taken to ensure pH <2.0. The batch is settled for at least 1 hour and then the product containing aqueous layer split. THF is added to the aqueous layer and the batch is cooled to 0° C. Batch pH is carefully adjusted to 8-10 range using 50 wt % sodium hydroxide keeping the temperature below 30° C. The aqueous layer is split to waste, and organic layer is concentrated solvent-exchanged to isopropyl alcohol. The batch is passed twice through CUNO® cartridges containing DARCO®-G60. The batch is heated to 75° C. and 48% hydrobromic acid solution (98 g) is added slowly. The batch is heated to reflux (80-85° C.) and agitated for 3-5 hours until the start of product crystallization. The batch was slowly cooled to 15° C. over 4 hours, held at 15° C. for 1 hour and then filtered. Isolated cake was washed twice with isopropyl alcohol (170 mL total) and dried under vacuum at 60° C. Obtained 100.4 g of compound VIII as an off-white solid. m.p.: 176° C. by DSC. $^1$H NMR (400 MHz, CDCl$_3$) δ 7.31 (m, 1H), 7.05 (m, 1H), 6.91 (m, 1H), 6.82 (m, 1H), 3.86 (br d, J=12.0 Hz, 1H), 3.67 (m, 1H), 3.63 (d, J=10.5 Hz, 1H), 2.75 (br m, 5H), 2.50 (m, 2H), 2.25 (m, 2H), 2.15 (m, 1H), 2.02 (s, 2H), 1.30 (m, 3H), 1.10 (m, 6H), 0.95 (m, 2H). MS (ESI) for M+H calcd. 396. found 396.

Example 7

Preparation of Compound of formula IX from compound of formula VIII and compound of formula B: Compound VIII (100 g, 179 mmol) is suspended in ethyl acetate (1000 mL) and treated with a solution of aqueous potassium carbonate (52 g, 2.1 eq, in 500 mL water). The aqueous layer is split off at 35-45° C. and the organic layer is washed with water at 35-45° C. The organic layer is azetropically dried and mixed with compound B (42 g, 1 eq) and acetone cyanohydrin (18 g, 1.2 eq). The resulting mixture is concentrated atmospherically to 300 mL over 8-10 hours. The concentrate is diluted with ethyl acetate (900 mL) and filtered through a bed of Celite (10 g). The filtrate is atmospherically concentrated to 400 mL and heptane (150 mL) containing compound IX seeds is added at reflux. After heated at reflux for 1 hour, additional heptane (150 mL) is added at reflux. The resulting slurry is heated at reflux for 1 hour and cooled over 1 hour to room temperature. After stirring at room temperature for 1 hour, the slurry is filtered and washed with 1:1 ethyl acetate/heptane (200 mL). The wet cake is dried at 45° C. under vacuum overnight to give a white solid (96 g, 84% yield). m.p.: 185° C. by DSC. $^1$H NMR (400 MHz, CDCl$_3$): δ 8.98 (s, 1H), 7.29 (dt, J$_1$=7.8 Hz, J$_2$=6.1 Hz, 1H), 6.97 (dt, J$_1$=8.4 Hz, J$_2$=2.1 Hz, 1H), 6.87 (d, J=7.6 Hz, 1H), 6.80 (br d, J=9.7 Hz, 1H), 4.53 (br d, J=14.2 Hz, 1H), 3.87 (br d, J=12.0 Hz, 1H), 3.66 (m, 2H), 3.32 (m, 2H), 3.22 (m, 1H), 2.60-2.95 (m, 5H), 2.41 (s, 3H), 2.37 (s, 3H), 2.35 (m, 1H), 2.22 (m, 4H), 2.05 (m, 4H), 1.65 (m, 1H), 1.55 (m, 1H), 1.30 (m, 2H), 1.15 (m, 6H), 0.95 (m, 2H), MS (ESI) for M+H calcd. 638. found 638.

Example 8

Preparation of Compound of formula I from compound of formula IX: To a solution of compound IX (250.0 g, 393 mmol) in tetrahydrofuran (1250 mL) cooled to 15-25° C. was added ~20 wt % of trimethyl aluminum in toluene (500 mL, 530 mmol). To the resulting homogeneous solution was slowly added 3.0M methyl magnesium chloride in tetrahydrofuran (325 mL, 510 mmol) at 15-25° C. The reaction mixture was stirred for 4 hours and then quenched in 10% aqueous sodium citrate solution (1575 mL) maintained at 35-45° C. The organic layer was washed with 10% aqueous sodium citrate solution (550 mL). The organic layer was washed with 1.5M aqueous HCl (442 ml). The aqueous acidic layer was digested at 35-45° C. for 4 hours and then cooled to 15-25° C. The aqueous layer was neutralized with 25% aqueous NaOH (119 mL) and then extracted into isopropyl acetate (1250 mL). The organic layer was washed with water (500 mL) and then evaporated under vacuum to give a foam. The yield was 96%. $^1$H NMR (400 MHz, CDCl$_3$): δ 8.6 (s, 1H); 7.3 (t, J=6.2 Hz, 1H); 7.0 (t, J=7.2 Hz, 1H); 6.9 (d, J=7.5 Hz, 1H); 6.8 (d, J=8.6 Hz, 1H); 4.0 (br, 1H); 3.8 (br, 1H); 3.6 (br m, 2H); 3.3 (t, J=11.0 Hz, 1H); 3.2 (t, J=11.0 Hz, 1H); 2.7 (br m, 5H); 2.5 (br, 1H); 2.4 (s, 3H); 2.3 (s, 3H); 2.2 (br m, 5H); 1.9 (br m, 3H); 1.7 (br, 1H); 1.4 (br m, 3H); 1.1 and 1.0 (br m, 7H); 0.93 (m, 2H), 0.88 (s, 3H). MS (ESI) for M+H calcd. 627. found 627.

While the EXAMPLES are described herein as the preparation of the compounds indicated, it will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A process for preparing a compound of formula (I)

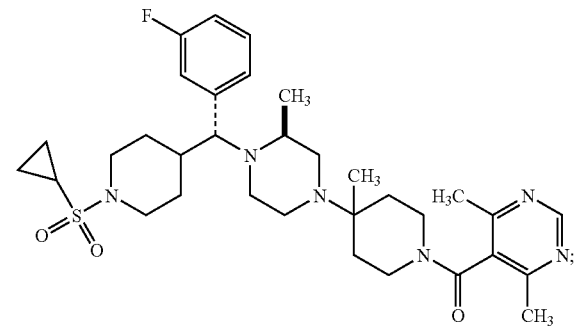

from a compound of formula V:

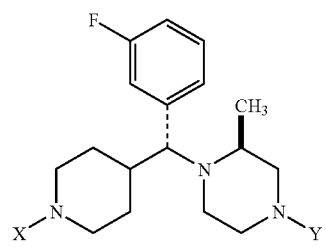

where X and Y are suitable protective moieties, wherein said process comprises:

(a) selectively removing the X protecting group of the compound of formula V to produce a compound of formula VI:

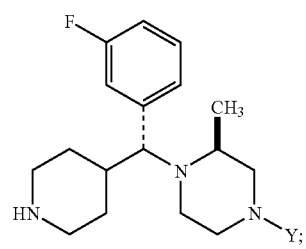

(b) sulfonylating the compound of formula VI with a cyclopropyl sulfonyl moiety, where W is a first leaving group:

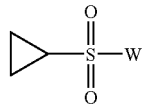

to form the compound of formula VII:

VII

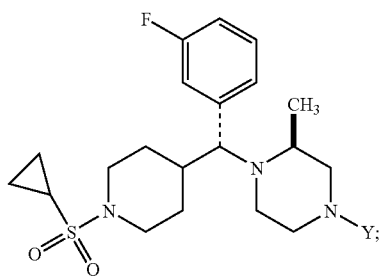

(c) removing the Y protecting group from the compound of formula VII and reacting with hydrogen bromide to produce the di-hydrobromide salt formula VIII:

VIII

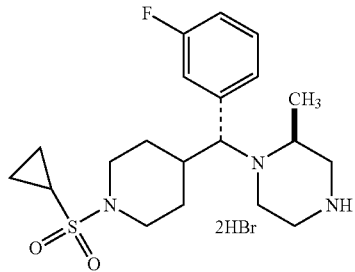

(d) reacting the compound of formula VIII with (i) an agent containing a leaving group G where G is a second leaving group selected from the group consisting of CN, Z, alkylsulfonates, OCOCZ$_3$ and benzotriazolyl, with Z being a halogen; and (ii) the compound of Formula VIIIa:

Formula VIIIa

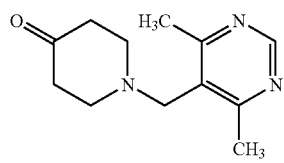

to form the compound of formula IX:

IX

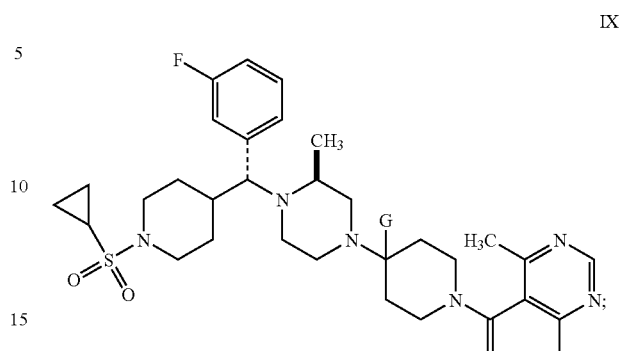

and (e) reacting the compound of formula IX with a Grignard reagent in a suitable solvent, followed by workup, to yield the compound of formula I, with the proviso that X and Y are different such that X may be selectively removed.

2. The process according to claim 1, wherein X is selected from the group consisting of: p-methoxybenzyl (PMB), allyl, methoxymethyl, benzyloxymethyl, trityl, pivaloyloxymethyl, tetrahydranyl, benzyl, di(p-methoxyphenyl)methyl, triphenylmethyl, (p-methoxyphenyl)-diphenylmethyl and t-butyl carbamate ("t-Boc").

3. The process according to claim 2, wherein X is p-methoxybenzyl (PMB):

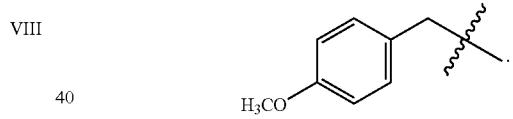

4. The process according to claim 1, wherein Y is selected from the group consisting of: carbobenzyloxy (Cbz), CZ$_3$CO (where Z is a halogen), 2-trimethylsilylethyl carbamate, 1-methyl-1-phenylethyl carbamate, t-butyl carbamate, cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, methyl carbamate, ethyl carbamate, diphenylphosphinyl, benzenesulfenyl, or acyl.

5. The process according to claim 4, wherein Y is carbobenzyloxy (Cbz):

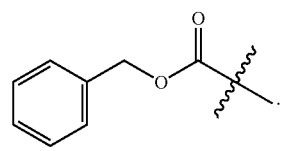

6. The process of claim 1, wherein W is a halide or triflate.

7. The process according to claim 6, wherein W is Cl.

8. A process for preparing a compound of formula IX:

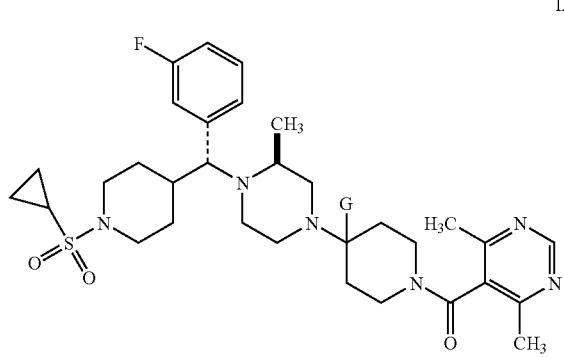

from a compound of formula VIII

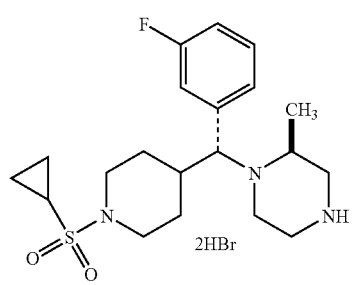

said process comprising reacting the compound of formula VIII with (I) an agent containing a leaving group G where G is a leaving group selected from the group consisting of CN, Z, alkylsulfonates, OCOCZ$_3$ and benzotriazolyl, with Z being a halogen, and (ii) the compound:

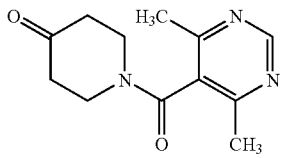

to form the compound of formula IX.

9. A process of preparing a compound of formula I:

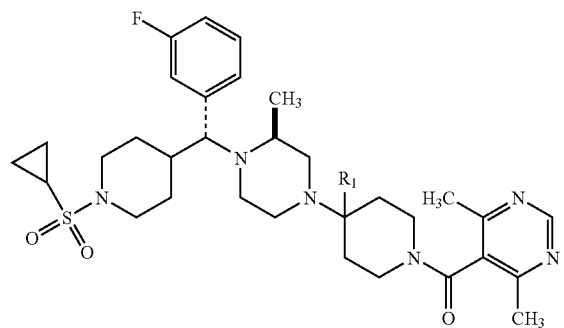

where R$_1$ is alkyl or aryl from a compound of formula IX:

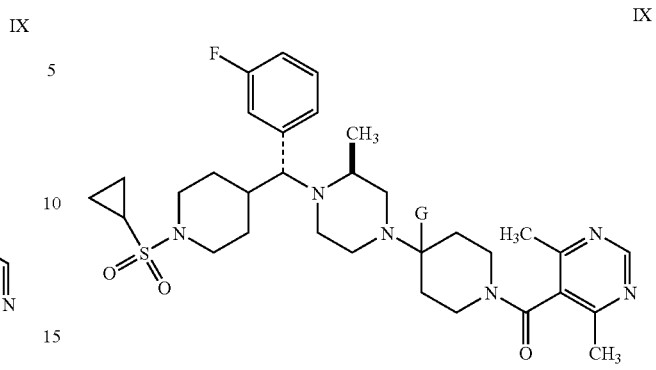

where G is a leaving group selected from the group consisting of CN, Z, alkylsulfonates, OCOCZ$_3$ and benzotriazolyl, with Z being a halogen,
said process comprising reacting the compound of formula IX with a Grignard reagent in a suitable solvent, followed by workup, to yield the compound of formula I.

10. The process of claim 1, wherein said deprotection in step (a) is performed using trifluoroacetic anhydride.

11. The process of claim 1, wherein said deprotection in step (a) is performed using 2,3-dichloro-5,6-dicyano-1,4-benzoquinone.

12. The process of claim 1, wherein said deprotection in step (c) is performed using methanesulfonic acid.

13. The process of claim 1, wherein said deprotection in step (c) is performed using a strong acid selected from the group consisting of sulfuric acid, hydrochloric acid and hydrobromic acid.

14. The process of claim 1, wherein step (d) comprises (1) converting said compound of formula VIII to a free base by use of a basic compound and (2) reacting said free base with an agent containing a leaving

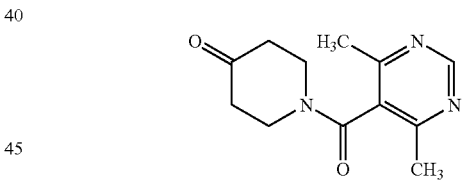

group G where G is a leaving group selected from the group consisting of CN, Z, OSO$_2$R$_2$, OCOCZ$_3$ and benzotriazolyl, with R$_2$ being an alkyl or aryl group and Z is a halogen.

15. The process of claim 14, wherein said agent containing a leaving group is a cyanating agent and is selected from the group consisting of: HCN, acetone cyanohydrin; cyclohexanone cyanohydrin; a mixture of (C$_2$H$_5$)$_2$AlCN and Ti(OPr)$_4$, a mixture of acetic acid, H$_2$SO$_4$; NaHSO$_4$, KHSO$_3$ or Na$_2$S$_2$O$_5$ and a cyanide source such as NaCN or KCN; trimethylsilylcyanide; glycolonitrile; mandelonitrile; glycinonitrile; acetone amino nitrile; and dimethylaminoacetonitrile.

16. The process of claim 15, wherein said cyanating agent is acetone cyanohydrin.

17. The process of claim 16, wherein said acetone cyanohydrin is used in about 1-5 molar equivalents with respect to the compound of formula VIII.

18. The process of claim 14, wherein is used in about 1-4 molar equivalents with respect to the compound of formula VIII.

19. The process of claim 14, wherein said basic compound is selected from:
(i) a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium;
(ii) a metal salt of a $C_1$-$C_{12}$ alkanol, a $C_3$-$C_{12}$ cycloalkanol, a ($C_3$-$C_8$ cycloalkyl)$C_1$-$C_6$ alkanol;
ammonia, a $C_1$-$C_{12}$ alkylamine, a di($C_1$-$C_{12}$ alkyl)amine, a $C_3$-$C_8$ cycloalkylamine, a N—($C_3$-$C_8$ cycloalkyl)-N—($C_1$-$C_{12}$ alkyl)amine, a di($C_3$-$C_8$ cycloalkyl)amine, a ($C_3$-$C_8$ cycloalkyl)$C_1$-$C_6$ alkylamine, a N—($C_3$-$C_8$-cycloalkyl)$C_1$-$C_6$-alkyl-N—($C_1$-$C_{12}$ alkyl)amine, a N—($C_3$-$C_8$ cycloalkyl)$C_1$-$C_6$ alkyl-N—($C_3$-$C_8$ cycloalkyl)amine, a di[($C_1$-$C_6$ cycloalkyl)$C_1$-$C_6$ alkyl]amine; or
(iii) a heterocyclic amine selected from the group consisting of imidazole, triazole, pyrrolidine, piperidine, heptamethyleneimine, morpholine, thiomorpholine and a 1-($C_1$-$C_4$ alkyl)piperazine.

20. The process of claim 19, wherein said basic compound is KOH, NaOH, $Na_2CO_3$, $K_2CO_3$, $NaHCO_3$, $KHCO_3$, tetramethylguanidine, DBU, diisopropylethylamine or mixtures thereof.

21. The process of claim 20, wherein said basic compound is $Na_2CO_3$ or $K_2CO_3$.

22. The process of claim 21, wherein said basic compound is $K_2CO_3$.

23. The process of claim 1, wherein said Grignard reagent in step (e) is selected from the group consisting of MeMgCl, MeMgBr and MeMgI.

24. The process of claim 23, wherein said Grignard reagent is MeMgCl.

25. The process of claim 24, wherein said MeMgCl is used in about 1-4 molar equivalents with respect to the compound of formula III.

26. The process of claim 1, wherein said solvent in step (e) is selected from the group consisting of hydrocarbons, halogenated hydrocarbons, ethers, and mixtures thereof.

27. The process of claim 26, wherein said solvent is selected from toluene, xylene, chlorobenzene, or dichlorobenzene alone or in admixture with a solvent selected from the group consisting of a $C_5$-$C_{12}$ alkyl ether, 1,2-dimethoxyethane, 1,2-diethoxyethane, diglyme, 1,4-dioxane and tetrahydrofuran.

28. The process of claim 1, wherein said work-up in step (e) is treatment with an acid in an aqueous phase.

29. The process of claim 28, wherein said acid is HCl.

30. The process of claim 28, wherein said acid is a strong acid selected from the group consisting of hydrobromic acid, sulfuric acid, and phosphoric acid.

31. The process of claim 8, wherein said agent containing a leaving group is a cyanating agent selected from the group consisting of: HCN, acetone cyanohydrin; cyclohexanone cyanohydrin; a mixture of $(C_2H_5)_2AlCN$ and $Ti(OPr)_4$, a mixture of acetic acid, $H_2SO_4$; $NaHSO_4$, $KHSO_3$ or $Na_2S_2O_5$ and a cyanide source such as NaCN or KCN; trimethylsilylcyanide; glycolonitrile; mandelonitrile; glycinonitrile; acetone amino nitrile; and dimethylaminoacetonitrile.

32. The process of claim 31, wherein said cyanating agent is acetone cyanohydrin.

33. The process of claim 9, wherein said Grignard reagent is methyl magnesium chloride.

34. The process of claim 9, wherein said solvent is a mixture of toluene and tetrahydrofuran.

35. A process for preparing a compound of formula (I)

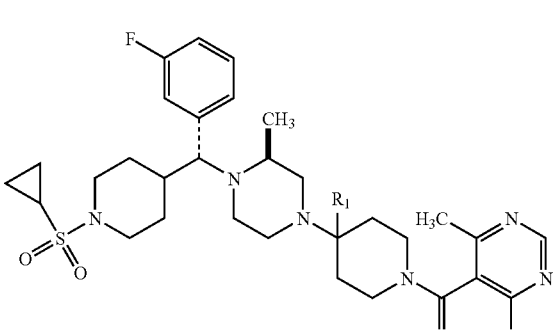

where $R_1$ is an alkyl or aryl group;
from a compound of formula II:

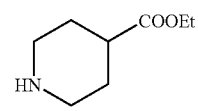

said process comprising:
(a) converting the compound of formula II to a compound of formula III by reacting with a reagent that introduces a PMB group:

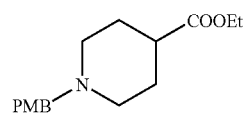

where PMB is p-methoxybenzyl;
(b) reacting said compound of formula III with a suitable reducing reagent, followed by purification through formation of a bisulfite salt and subsequent treatment with a basic compound, to yield a compound of formula IV:

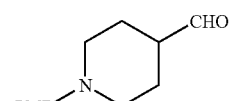

(c) reacting said compound of formula IV with benzotriazole, 3-fluorophenylmagnesium bromide and the compound:

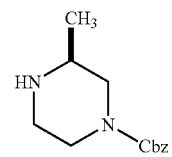

to yield a compound of formula V, where Cbz is carbobenzyloxy

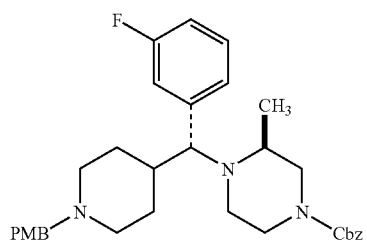

V;

(d) removing the PMB protecting group of the compound of formula V to produce a compound of formula VI:

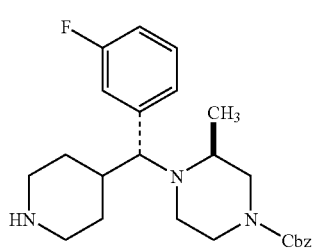

VI;

(e) sulfonylating the compound of formula VI with cyclopropyl sulfonyl chloride, to form the compound of formula VII:

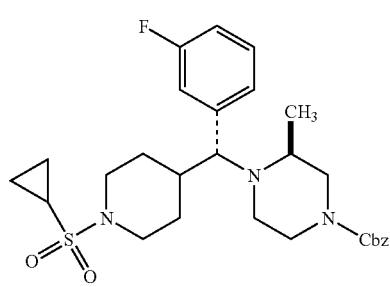

VII;

(f) removing the Cbz protecting group from the compound of formula VII and reacting with hydrogen bromide to produce the di-hydrobromide salt formula VIII:

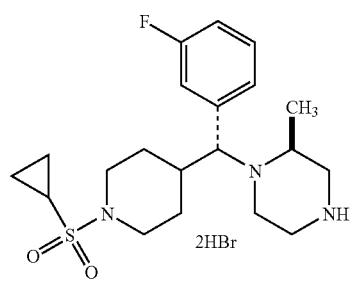

VIII;

(g) reacting the compound of formula VIII with (i) an agent containing a leaving group G where G is a leaving group selected from the group consisting of CN, Z, $OSO_2R_2$, $OCOCZ_3$ and benzotriazolyl, with $R_2$ being an alkyl or aryl group and Z is a halogen; and (ii) the compound:

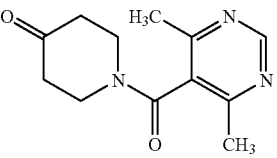

to form the compound of formula IX:

IX;

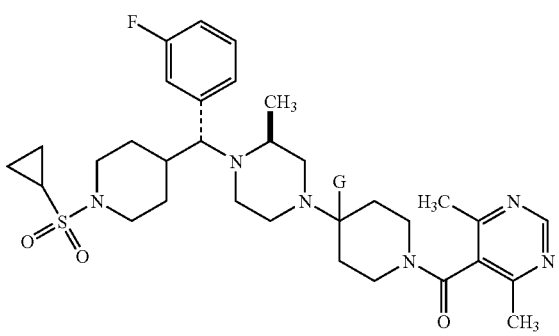

and (h) reacting the compound of formula IX with a Grignard reagent in a suitable solvent followed by a workup to yield the compound of formula I.

36. A compound, including isomers of said compound, of the formula:

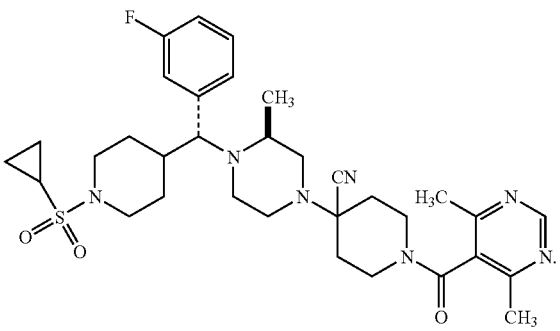

* * * * *